(12) United States Patent
Wiktor

(10) Patent No.: US 9,068,965 B2
(45) Date of Patent: Jun. 30, 2015

(54) APPARATUS AND METHOD FOR DETECTING BLOOD CLOTS IN AN EXTRACORPOREAL BLOOD CIRCUIT

(75) Inventor: Christoph Wiktor, Gelnhausen (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 103 days.

(21) Appl. No.: 13/817,651

(22) PCT Filed: Aug. 12, 2011

(86) PCT No.: PCT/EP2011/004072
§ 371 (c)(1),
(2), (4) Date: Feb. 19, 2013

(87) PCT Pub. No.: WO2012/022456
PCT Pub. Date: Feb. 23, 2012

(65) Prior Publication Data
US 2013/0155387 A1 Jun. 20, 2013

(30) Foreign Application Priority Data

Aug. 17, 2010 (DE) .......................... 10 2010 034 553

(51) Int. Cl.
*G01N 33/48* (2006.01)
*G01N 33/49* (2006.01)
*A61M 1/36* (2006.01)
*G01N 29/02* (2006.01)

(52) U.S. Cl.
CPC ............ *G01N 33/49* (2013.01); *A61M 1/3626* (2013.01); *A61M 1/367* (2013.01); *A61M 2205/3306* (2013.01); *A61M 2205/3313* (2013.01); *A61M 2205/3375* (2013.01); *G01N 29/02* (2013.01)

(58) Field of Classification Search
CPC ...................................................... G01N 33/49
USPC ............................................................ 356/39
See application file for complete search history.

(56) References Cited

U.S. PATENT DOCUMENTS

| 3,935,876 | A | | 2/1976 | Massie et al. | |
|---|---|---|---|---|---|
| 3,974,681 | A | * | 8/1976 | Namery | 73/600 |
| 4,122,713 | A | * | 10/1978 | Stasz et al. | 73/861.25 |
| 4,690,002 | A | * | 9/1987 | Hubbard et al. | 73/861.25 |
| 4,944,189 | A | * | 7/1990 | Nakajima et al. | 73/861.25 |
| 5,043,706 | A | * | 8/1991 | Oliver | 340/603 |
| 5,394,732 | A | * | 3/1995 | Johnson et al. | 73/19.1 |
| 5,670,050 | A | * | 9/1997 | Brose et al. | 210/646 |
| 6,413,233 | B1 | * | 7/2002 | Sites et al. | 604/6.13 |
| 6,529,751 | B1 | * | 3/2003 | Van Driel et al. | 600/322 |
| 6,542,761 | B1 | | 4/2003 | Jahn et al. | |

(Continued)

FOREIGN PATENT DOCUMENTS

| EP | 0 980 686 | 2/2000 |
|---|---|---|
| EP | 0 979 111 | 2/2006 |

(Continued)

*Primary Examiner* — Roy M Punnoose
(74) *Attorney, Agent, or Firm* — Jacobson Holman, PLLC.

(57) ABSTRACT

An apparatus for detecting blood clots in a blood stream of an extracorporeal blood circuit includes an optical sensor, an ultrasound sensor, and a signal evaluator. The apparatus is configured such that the blood is optically monitored by the optical sensor and ultrasonically monitored by the ultrasound sensor. The signal evaluator is configured such that the blood clots are detected by a comparison of the monitoring signals of the optical sensor and the ultrasound sensor.

21 Claims, 3 Drawing Sheets

(56) References Cited

U.S. PATENT DOCUMENTS

| | | | |
|---|---|---|---|
| 6,740,036 B1 * | 5/2004 | Lee et al. | 600/437 |
| 7,170,591 B2 * | 1/2007 | Ohishi et al. | 356/39 |
| 7,523,649 B2 * | 4/2009 | Corey et al. | 73/61.75 |
| 7,758,532 B2 * | 7/2010 | Mori et al. | 604/5.01 |
| 2004/0057037 A1 * | 3/2004 | Ohishi et al. | 356/39 |
| 2006/0287628 A1 | 12/2006 | Hirabuki | |
| 2007/0266778 A1 * | 11/2007 | Corey et al. | 73/61.75 |
| 2009/0078047 A1 * | 3/2009 | Dam | 73/606 |

FOREIGN PATENT DOCUMENTS

| | | |
|---|---|---|
| JP | 7-103967 | 4/1995 |
| WO | WO 2007/121398 | 10/2007 |

* cited by examiner

APPARATUS AND METHOD FOR DETECTING BLOOD CLOTS IN AN EXTRACORPOREAL BLOOD CIRCUIT

CROSS-REFERENCE TO RELATED APPLICATIONS

This is a national stage of PCT/EP11/004072 filed Aug. 12, 2011 and published in German, which has a priority of German no. 10 2010 034 553.9 filed Aug. 17, 2010, hereby incorporated by reference.

BACKGROUND OF THE INVENTION

1. Field of Invention

The present invention relates to an apparatus for determining and/or monitoring foreign structures in a fluid or in a fluid flow as well as in particular to a method herefor.

2. Description of the Prior Art

It is of importance in an extracorporeal blood circuit such as a hemodialysis system that blood is monitored with respect to dangerous components which can arise by the treatment. Strict care must in particular be taken that gas bubbles and blood clots in the extracorporeal blood circuit can be recognized and/or held back. Known treatment systems are in this respect in a position to react to the recognition of air bubbles and to effect a corresponding alarm and/or treatment stop. It is furthermore attempted to hold back blood clots by means of clot catchers.

Prevalent examinations of blood samples with respect to their components or their flow characteristic can e.g. take place using ultrasound measurements based on different principles or by optical measurements. Gas bubbles in the blood can e.g. be recognized by correspondingly adjusted frequencies using an ultrasound analysis. The occurrence of blood clots can, in contrast, not be detected using the same ultrasound principle since the scattering of the sound at the clots is too small as a rule. It can also be the case that the density difference in the blood section of clots cannot be distinguished from other sections. Optical measurements can recognize the occurrence of clots by a change in the transmission of light. Clots cannot, however, simultaneously be distinguished from gas bubbles which likewise cause an increase in transmission.

It is problematic that, despite anticoagulation, it is not precluded that blood clots occur in the extracorporeal blood circuit of a dialysis machine. The reasons for this can be varied and the incorrect dosage of anticoagulants such as heparin or citrate is not always the cause. Hemostasis, stagnation zones and the contact with air or with the artificial surfaces of the extracorporeal blood circuit promote an activation of the coagulation cascade.

The thrombocytes or blood platelets in the blood change their shape after the activation of coagulation and aggregate to thrombi. These thrombi can clog the capillaries of the dialyzer and, if they are not caught in the extracorporeal blood circuit, enter into the patient's circulation and close smaller vessels there. For this reason, there are venous clot catchers in many current blood tube and cassette systems which should catch blood clots before they enter into the body of the patient. This protective measure is, however, not without controversy.

If it is intended to return the blood not through the vein, but through the artery after a dialysis treatment, a mechanical clot catcher at the arterial side does not provide any remedy since clots previously trapped are released again on the flow reversal and can enter into the patient.

Some approaches are already known from the prior art for monitoring a fluid flow for gas bubbles or solid bodies which arise therein.

U.S. Pat. No. 4,122,713, for example, discloses a measurement system for determining the flow speed of a fluid. In this respect, the system is also able to determine the presence of air bubbles in the blood in addition to the measurement of the blood flow speed.

EP 0 979 111 B1 relates to an apparatus for the optical recognition and quantification of microbubbles. In this respect, an optical recognition of blood clots is described which can, however, in this form only be accepted by particles of a corresponding size, but not for small blood clots.

JP 7103967 describes an arrangement for examining blood serum samples which are located in a sample vessel such as e.g. a measuring cup. A level measurement and a phase boundary detection of separated blood samples located in the sample vessels is carried out by means of optical sensors and an ultrasound sensor.

A system is furthermore known from WO 2007/121398 A2 for detecting gas bubbles and solid particles in blood by radio wave analysis.

U.S. Pat. No. 3,935,876 discloses an apparatus for monitoring a blood flow with respect to air bubbles using optical means, wherein a monitoring for blood clots can take place simultaneously using the apparatus.

Despite the previous approaches, it would be desirable also to recognize the occurrence of blood clots, in particular also small blood clots, as well as gas bubbles in blood fast and reliably, wherein a corresponding measurement device has as simple a structure as possible.

SUMMARY OF THE INVENTION

It is therefore the object of the present invention to further develop an apparatus and a method of the initially named kind in an advantageous manner, in particular such that a simpler and more reliable method as well as an apparatus which can be operated simply and reliably are provided, wherein a secure and highly precise monitoring of a blood flow is advantageously possible with respect to air bubbles and blood clots.

This object is achieved in accordance with the invention by an apparatus as described herein. Provision is accordingly made that an apparatus for determining and/or monitoring foreign structures in a fluid or in a fluid flow is provided with at least one optical monitoring means, at least one ultrasound monitoring means and at least one signal evaluation means, wherein the fluid can be optically monitored at least by means of the optical monitoring means and at least by means of ultrasound by means of the ultrasound monitoring means, and wherein at least one foreign structure, in particular an air bubble and/or a solid body such as a blood clot, can be recognized in the fluid with reference to the combination of the monitoring signals obtained herefrom by means of the signal evaluation means and/or can be distinguished from at least one second foreign body structure by means of the signal evaluation means.

The fluid can in particular be blood and the fluid flow can in particular be a blood flow.

The combination of the monitoring signals for recognizing the at least one foreign structure or for distinguishing the first foreign structure from at least one second foreign structure can preferably take place with reference to the comparison of the monitoring signals of the optical monitoring means and of the ultrasound monitoring means.

The foreign structure can, for example, be an air bubble and/or a solid body such as a blood clot; such an air bubble in particular represents a first foreign structure and a solid body such as a blood clot represents a second foreign structure which can be recognized and distinguished by means of the apparatus.

If a foreign structure is detected by means of the ultrasound monitoring means, an air bubble is hereby recognized, and indeed generally also independent of whether this is likewise detected by means of the optical monitoring means. In the normal case and preferably, an air bubble is detected both by the ultrasound monitoring means and by the optical monitoring means. This is, however, not absolutely necessary for the detection of air bubbles.

The advantage thereby results of being able to use monitoring methods operating simply and reliably, namely an optical monitoring means and an ultrasound monitoring means. In the optical monitoring means, the measurement principle of, for example, a simple transmission measurement can be utilized. In the ultrasound monitoring, generally all measurement principles are possible by which e.g. gas bubbles can be detected.

For example, the receiver part of the ultrasound monitoring means can be arranged at a side of a fluid guidance path. The ultrasonic pulse can then be coupled by a transmitter into the fluid guide flowed through by liquid. The gas bubbles in the fluid attenuate the acoustic signal. After the acoustic signal passes through the fluid guide, the signal is incident onto the wall of the fluid guidance passage and is reflected correspondingly. This signal then again passes through the fluid guide and can be taken up by the receiver part. A distinction can then be made with reference to the evaluation of the acoustic signal as to whether gas bubbles are present or not.

It is advantageously possible by the combined evaluation of the monitoring signals which can be obtained by the optical monitoring means and by the ultrasound monitoring means to recognize the presence of an air bubble and/or of a solid body simply and reliably.

A corresponding signal evaluation means can, for example, be a calculating unit, with it also being able to be the calculating unit of a control and/or regulation means, which is in communication with the apparatus, of a blood treatment apparatus such as a hemodialysis machine.

Provision can furthermore be made that one or more air bubbles in the fluid can be recognized by means of the signal evaluation means when at least the ultrasound monitoring means registers at least one foreign body as a signal-triggering event and outputs a signal or when the optical monitoring means and the ultrasound monitoring means each substantially simultaneously register at least one foreign structure as a signal-triggering event and output a signal, and/or that one or more solid bodies, in particular blood clots, in the fluid can be recognized by means of the signal evaluation means when the optical monitoring means registers at least one foreign structure as a signal-triggering event and the ultrasound monitoring means substantially simultaneously does not register any foreign structure, or recognizes a very small foreign structure, as a signal-triggering event. A simultaneous measurement can understandably only take place when the optical monitoring means and the ultrasound monitoring means are arranged at the same location or register signal-triggering events at the same location. If the optical monitoring means and the ultrasound monitoring means are not arranged at the same location, but rather offset, or if they register signal-triggering events at different locations, this offset hasto be taken into account e.g. by taking account of the flow speed and of the dead time associated with it. The registration of the signal-triggering events also takes place in such a case likewise substantially simultaneously in the aforesaid sense by the taking into account of the offset. Optical monitoring means and the ultrasound monitoring are in particular preferably arranged only with a small or very small offset. It is also conceivable in this connection that a clot can be recognized when the optical signal is substantially larger or stronger than the received ultrasound signal. A clot can thus likewise be detected with reference to the divergence of the signals obtained.

It is possible that the optical monitoring means is at least one optical sensor or includes at least one optical sensor and/or that the ultrasound monitoring means is at least one ultrasound sensor or includes at least one ultrasound sensor and/or that air bubbles and solid bodies, in particular blood clots, can be detected by means of the optical monitoring means and air bubbles can be detected by means of the ultrasound monitoring means. The optical sensor can react to air bubbles and equally to blood clots by a short and strong signal increase since the transmitted intensity of the radiation briefly increases. In contrast, an ultrasound sensor can only detect and quantify air bubbles flowing past. Clot recognition cannot take place by the ultrasound sensor since the density difference between the blood or plasma and the clot is too small. Consequently, in a case in which only the optical sensor generates a signal and the ultrasound sensor does not generate any signal, it can be found that a blood clot is present in the bloodstream. Accordingly, one or more air bubbles can be detected when both sensors, that is, the optical sensor and the ultrasound sensor, generate a signal.

Provision can preferably be made that the optical sensor has at least one light source and at least one photodetector, wherein the light source preferably is or includes at least one LED and/or wherein narrowband, near infrared light with a peak wavelength of approximately 805 nm can particularly advantageously be radiated by means of the light source. The wavelength range around 805 nm is in particular very suitable for the optical sensor for clot detection since the absorption by the hemoglobin in the erythrocytes is very small, on the one hand, and is independent of the oxygen content, on the other hand. The signal generation is consequently advantageously liberated from corresponding disturbance factors and signal falsifications.

Thrombocytes have a very low absorption coefficient (not measurable) at 805 nm; however, scattering takes place at the cells which (as with erythrocytes) is substantially forward scattering. In the normal case (without formation of thrombi), however, this scattering can be neglected since the number and size of the thrombocytes is very small in comparison with erythrocytes: 99% of the blood cells are erythrocytes having a diameter of approximately 7.5 µm (thrombocytes have a diameter of 1.5-3 µm). On the onset of coagulation, thrombocytes aggregate, form a thrombus and adopt a greater volume. This results in reduced absorption within the measurement path and thus in an increase in the transmitted radiation at 805 nm.

It is furthermore conceivable that down-signal of the optical monitoring means at least one high pass filter is arranged by means of which the monitoring signal acquired by means of optical monitoring can be filtered.

The high pass filter can advantageously be a filter in which the monitoring signal can be integrated at fixed intervals of a few milliseconds and a floating mean value can be determined from a predetermined number of preceding measurements and can be subtracted from the then current integration result. Such a filter has the advantage that it enables a simple evaluation of the signal. If, with such a filter, the integration result is given higher weighting than the low pass, a high boost filter is obtained which has the advantage that the basic signal profile is maintained, while the brief changes are emphasized. If the high pass filtered signal exceeds a threshold value, either an air bubble or a clot has flowed through the measurement path. If the ultrasound sensor likewise detects its own signal close in time while taking account of the flow speed, it is the case of an air bubble. If, however, the ultrasound sensor does not register anything, a clot was detected.

Generally, however, other high pass filters are also suitable for the evaluation.

It is moreover possible that the apparatus has a recipient into which a fluid guidance means, preferably a hose kit or a part of a hose kit or a cassette, in particular a disposable cassette, or a measurement channel can be inserted and/or that the apparatus comprises a measurement channel. Such a hose kit can in particular be the hose kit of an extracorporeal blood circuit for a hemodialysis machine. Furthermore, such a disposable cassette can be a disposable cassette in which parts of an extracorporeal blood circuit for a hemodialysis machine are arranged.

It is furthermore conceivable that the apparatus has or forms a limited measurement path or measurement point at which both the optical monitoring means and the ultrasound monitoring means are arranged. The monitoring for air bubbles and/or blood clots can be advantageously improved by the spatial proximity of the optical monitoring means to the ultrasound monitoring means.

It is particularly advantageous if the measurement path or measuring point is arranged in and/or at the recipient and/or that the measurement path or measurement point is surrounded by the light source, the ultrasound sensor and the photodetector of the optical monitoring means by three sides, preferably in this order, and advantageously arranged so that the light source, the ultrasound sensor and the photodetector of the optical monitoring means surround the measurement path or measurement point in a U shape. A very short measurement path can in particular be realized by the U-shaped arrangement of the light source, ultrasound sensor and photodetector, with the advantage that a comparatively highly precise monitoring of the measurement path is possible. The time offset between the respective generated signals of the optical monitoring means and of the ultrasound monitoring means is hereby kept as low as possible.

It is generally also conceivable that the optical monitoring means and the ultrasound monitoring means are arranged in transmission and in each case transverse to the direction of flow. It is further conceivable that the optical monitoring means is arranged in transmission transverse to the direction of flow and the ultrasound monitoring means is arranged longitudinally to the direction of flow.

Provision can furthermore be made that the apparatus has at least one protection means and/or at least one warning means and/or is in communication with at least one protection means and/or at least one warning means, wherein the fluid flow can preferably be stopped by means of the protection means and/or wherein attention can preferably be drawn to components recognized in the fluid, in particular air bubbles and solid bodies such as blood clots by means of the warning means. The warning means can be an acoustic warning means and/or an optical warning means, for example. Provision can in particular be made that a warning indication is output by means of the warning means, on a screen for instance, with a warning tone simultaneously being sounded. The protection means can be made, for example, as a clamp or can comprise a clamp and can simultaneously preferably cooperate with a drive means such as the pump of the fluid flow. It can thereby advantageously be ensured that when foreign structures are recognized in the fluid, the fluid flow can be stopped immediately and a corresponding warning can be output. This is in particular very important and of advantage in hemodialysis since a supply of air bubbles or blood clots to the patient can hereby be reliably suppressed.

The protection means and also the warning means can advantageously be components of a blood treatment apparatus such as of a hemodialysis machine which are generally anyway present as usual components in the blood treatment apparatus. The advantage thus results of being able to make use of already existing components so that existing blood treatment apparatus can be simply retrofitted.

Provision can furthermore be made that the apparatus is a component of a blood treatment apparatus, in particular of a hemodialysis machine, or that the apparatus is a blood treatment apparatus, in particular a hemodialysis machine.

The invention furthermore relates to a method for determining and/or monitoring foreign structures in a fluid or in a fluid flow having the features described herein. Provision is accordingly made that the fluid is monitored optically and by means of ultrasound for determining and/or monitoring foreign structures in a fluid or in a fluid flow, in particular blood or bloodstream, and wherein at least one foreign structure, in particular an air bubble and/or a solid body such as a blood clot, can be recognized in the fluid and/or can be distinguished from at least one second foreign structure with reference to the combination of the monitoring signals obtained herefrom, in particular with reference to the comparison of the monitoring signals obtained herefrom. It is in particular of advantage that a first foreign structure such as an air bubble can be distinguished simply, safely and reliably from a second foreign structure such as a blood clot by the method in accordance with the invention.

Provision can furthermore be made that one or more air bubbles are recognized in the fluid if at least one foreign structure is recognized in the fluid at least by ultrasound monitoring or if at least one foreign structure is recognized in the fluid substantially simultaneously by means of optical monitoring and ultrasound monitoring, and/or that one or more solid bodies, in particular blood clots, are recognized in the fluid when at least one foreign structure is optically recognized in the fluid and no foreign structures or a very small foreign structure are/is recognized by means of ultrasound. A simultaneous measurement can understandably only take place when the optical monitoring means and the ultrasound monitoring means are arranged at the same location or register signal-triggering events at the same location. If the optical monitoring means and the ultrasound monitoring means are not arranged at the same location, but rather offset, or if they register signal-triggering events at different locations, this offset has to be taken into account e.g. by taking account of the flow speed and of the dead time associated with it. The registration of the signal-triggering events also takes place in such a case likewise substantially simultaneously in the aforesaid sense by the taking into account of the offset. Optical monitoring means and the ultrasound monitoring are in particular preferably arranged only with a small or very small offset. It is also conceivable in this connection that a clot can be recognized when the optical signal is substantially larger or stronger than the received ultrasound signal. A clot can thus likewise be detected with reference to the divergence of the signals obtained.

It is furthermore advantageously possible that the monitoring signal acquired by means of optical monitoring is filtered by means of a high pass filter.

Any kind of high pass filter is generally suitable for this purpose.

It is, however, particularly advantageous if the high pass filter is preferably a filter in which the monitoring signal is integrated at fixed intervals of a few milliseconds and a floating mean value is determined from a predetermined number of preceding measurements and is subtracted from the then current integration result.

Provision can be made that the method is carried out using at least one apparatus as described herein.

The present invention furthermore relates to the use of an apparatus as described herein for carrying out the method described herein and/or to the use of an apparatus as described herein in a blood treatment apparatus, in particular in a hemodialysis machine.

The present invention furthermore relates to a blood treatment apparatus as described herein, in particular to such a blood treatment apparatus associated with a hemodialysis machine. Provision is accordingly made that a blood treatment device, in particular a dialysis machine, is provided with at least one apparatus as described herein.

The present invention furthermore relates to the use of a blood treatment apparatus as described herein. Provision is accordingly made that a blood treatment apparatus, in particular a blood treatment apparatus associated with a hemodialysis machine, is used for carrying out the method described herein and/or is used in a blood treatment apparatus, in particular in a hemodialysis machine.

The invention furthermore relates to a disposable having the features described herein. Provision is accordingly made that a disposable, in particular a disposable hose set or a disposable cassette, is employed for use in an apparatus as described herein, preferably for use in the recipient of the apparatus in which a fluid guidance element is inserted.

BRIEF DESCRIPTION OF THE DRAWINGS

Further details and advantages of the invention will be explained in more detail in the following in an embodiment of the invention shown in the drawing.

There are shown.

DETAILED DESCRIPTION OF THE PREFERRED EMBODIMENTS

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

Figure 1:
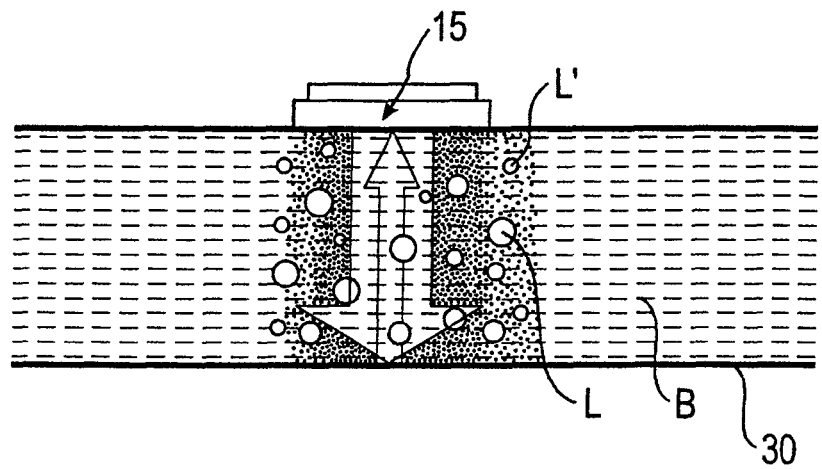
FIG. 1: a schematic representation of the detection of air bubbles by means of ultrasound.

FIG. 1 shows in a schematic representation the detection of air bubbles by means of ultrasound means of an ultrasound sensor 15 such as is used in the apparatus 10 for determining and monitoring air bubbles and blood clots.

As shown in FIG. 1, the ultrasonic pulse is coupled by the transmitter of the ultrasound sensor 15 into the fluid guide 30 which is flowed through by fluid and which can be a hose piece 30 of a disposable hose kit for hemodialysis not shown in more detail. Gas bubbles L, L' located in the blood B with different sizes attenuate this signal. After the sound signal has passed through, the signal is incident onto the wall of the fluid guide 30 disposed opposite the transmitter and is reflected. The reflected signal now passes through the fluid guide 30 a second time and is received by a receiver of the ultrasound sensor 15. It is now generally possible with reference to the evaluation of the sound signal to distinguish whether gas bubbles are present or not.

The ultrasound sensor 15 preferably combines the transmitter and the receiver in a common piezoelement by means of which the ultrasound signal can be output and received. A switchover is periodically made, for example, between transmission and reception in such an embodiment.

Figure 2:
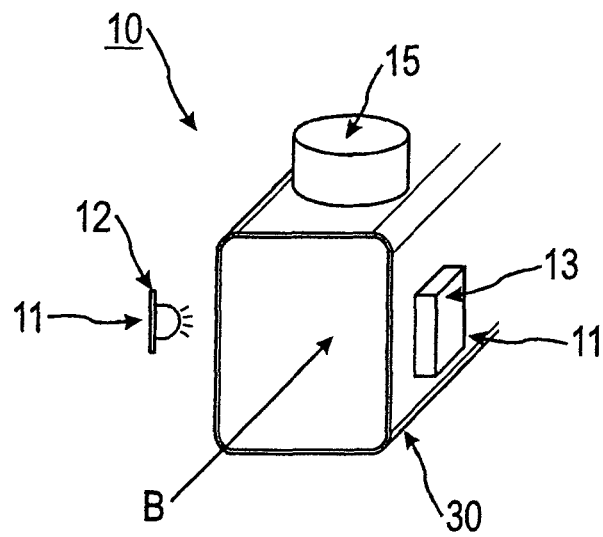
FIG. 2: a schematic representation of an apparatus in accordance with the invention for determining and monitoring air bubbles and blood clots in a bloodstream.

The optical sensor 11 for clot detection (clot detector 11) of the apparatus 10 substantially comprises, as can be seen in FIG. 2, an LED 12 as a light source 12 which radiates narrow band, near infrared light with a peak wavelength of approximately 805 nm. The wavelength range around 805 nm is in particular very suitable since the absorption by the hemoglobin in the erythrocytes (red blood cells) is very small, on the one hand, and is independent of the oxygen content, on the other hand.

A photodetector 13 for transmission measurement is arranged opposite this light source 12. This is preferably a photodetector 13 which outputs a frequency signal corresponding to the received intensity. Alternatively, a photodetector is, however, likewise possible which outputs a voltage proportional to the intensity or a current proportional to the intensity.

The measurement path is located between the light source 12 (transmitter) and the photodetector 13 (receiver). This measurement path can either be a clamped tube 30 or a channel of a cassette system. The blood B flows through this measurement path. The air bubble detector 15 on an ultrasound basis, which is ideally attached only at one side (cf. also FIG. 2) so that the measurement path is surrounded in U shape is located in direct proximity of the clot detector 11. The machine front of a blood treatment apparatus, such as of a hemodialysis machine, which is not shown in any more detail, is located at the opposite side of the air bubble detector 15.

The ultrasound sensor 15 detects and quantifies air bubbles flowing past. This sensor 15 cannot detect clots since the density difference between blood or plasma and clot is too small. The clot detector 11 reacts to air bubbles and equally to blood clots with a short, strong signal increase since the transmitting intensity of the radiation briefly increases. The signal of the photodetector 13 is integrated by an evaluation unit not shown in any more detail at fixed intervals of some ms for evolution. This is done in the detector with a frequency output by counting the pulses or by measuring the frequency. A floating mean value is determined from a specific number of preceding measurements and is subtracted from the then current integration result. This type of high pass filter enables a simple evaluation of the signal. Other high pass filters are, however, likewise suitable for the evaluation.

If the high pass filtered signal exceeds a threshold value, either an air bubble or a clot has flowed through the measurement path. If the ultrasound sensor 15 likewise detects an event (close in time while taking account of the flow speed), it is an air bubble. If, however, the ultrasound sensor 15 does not register anything, a clot was detected.

Figure 3:
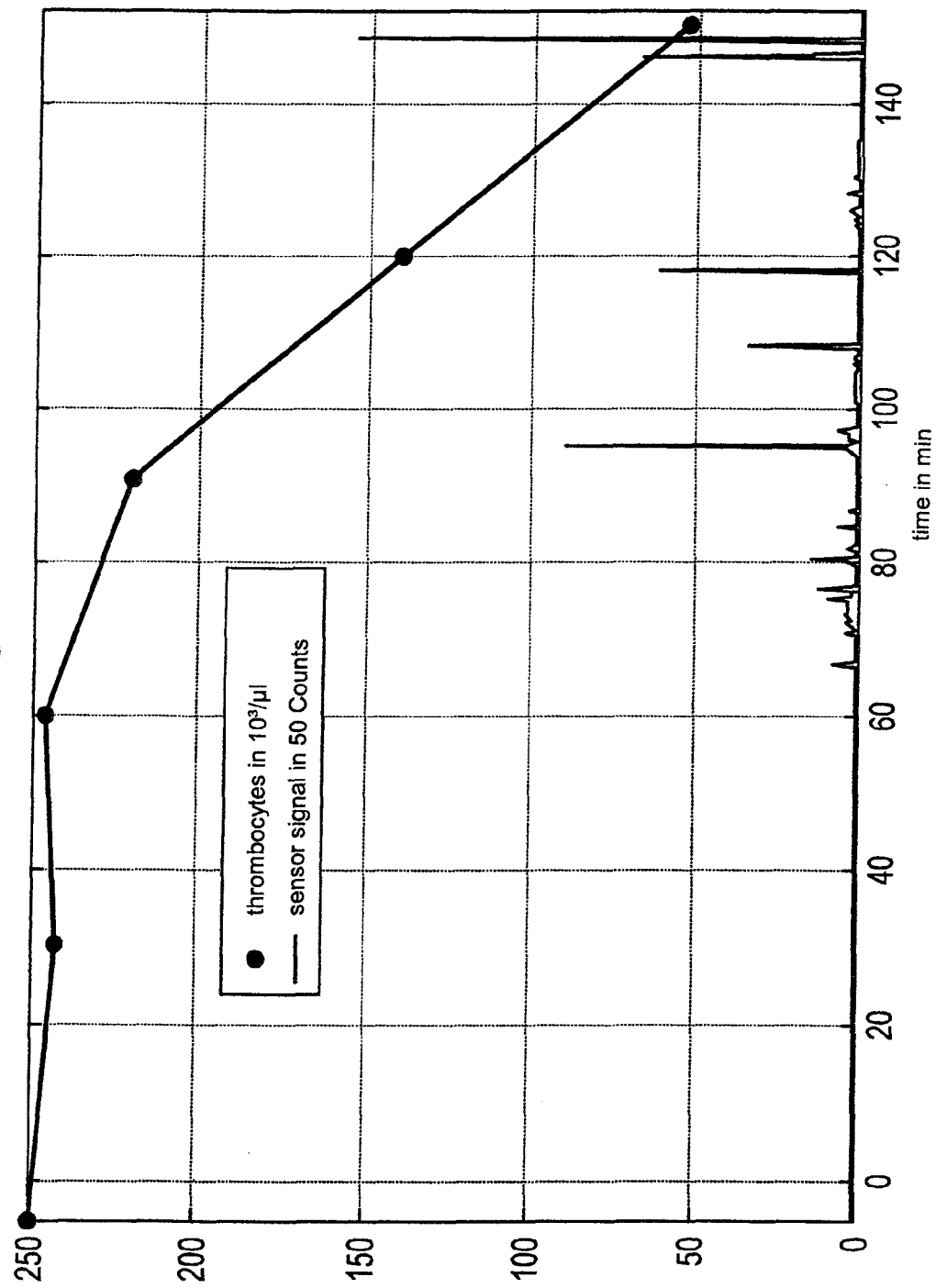
FIG. 3: a diagram relating to the detection of blood clots by means of the optical sensor.

FIG. 3 shows the event of a measurement with blood and with the optical sensor 11 by way of example. The coagulation of the blood occurs after a little more than 60 minutes, which can be detected from the decline in thrombocytes in the blood. A plurality of blood clots consequently occur which are detected by means of the sensor 11. The amplitudes of the sensor signal are entered into the diagram as perpendicular bars.

The level of the pulses can be influenced by the design of the sensor 11. In the case in question here, an integration of the sensor signal over 20 ms is carried out. If this integration time is selected as shorter, the pulses can be distinguished more clearly from the remaining transmission signal. The design of the filter or high pass filter—in particular the number of measured values which are taken into the calculation of the floating average—likewise influences this.

If now a clot or an air bubble is detected, an alarm is output by the blood treatment apparatus, in particular by the hemodialysis machine, for instance by a warning tone and by a corresponding display by means of a flashing warning light or on the operating screen.

Figure 4:
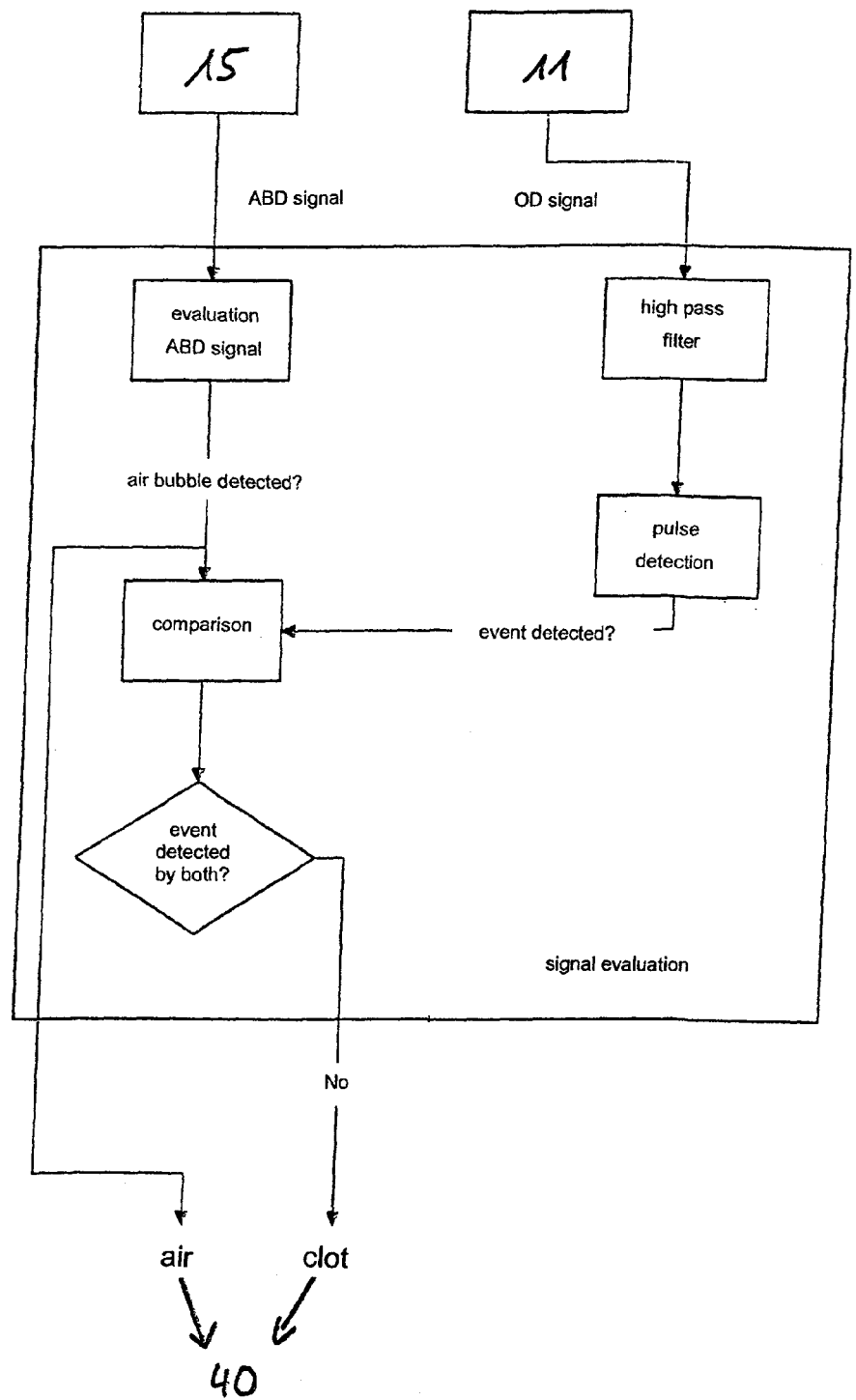
FIG. 4: a flow chart relating to the signal evaluation of the method and of the apparatus in accordance with the invention.

The apparatus in accordance with the invention can particularly advantageously be used in the reinfusion of blood from the extracorporeal blood circuit since in this process blood is not conveyed through the clot catcher usually present in the venous part in a compulsory manner. For example, in the case of an alarm during reinfusion, a termination of the reinfusion or an instigation of a special handling can be triggered by the operator, wherein the special handling can comprise the corresponding fluid flow with the clot or air bubbles being conveyed into a saline bag or into another collection container. Simultaneously, however, also no warning can be output for clots or air bubbles which are conveyed through the air catcher and clot catcher in the venous part of the extracorporeal blood circuit in the normal direction of flow since they do not represent any risk for the patient. These functions can preferably be carried out fully automatically or semiautomatically by a protection and warning means 40 (cf. FIG. 4).

It is, for example, conceivable that a respective optical sensor 11 and a respective ultrasound sensor 15 are provided both on the arterial side and on the venous side of the blood circuit. In normal treatment operation, the sensor pair comprising the optical sensor 11 and the ultrasound sensor 15 can be evaluated for clots on the venous side of the extracorporeal blood circuit and can require a special handling on a detection. In normal reinfusion, for example by means of a conveying of saline solution from a saline solution bag connected to the arterial line and of a reinfusion of the blood via the venous part of the extracorporeal blood circuit, the sensor pair comprising the optical sensor 11 and the ultrasound sensor 15 can be evaluated or is evaluated likewise on the venous side of the extracorporeal blood circuit. On a simultaneous reinfusion, that is, if the blood is returned both via the arterial and via the venous parts of the extracorporeal blood circuit, both sensor pairs, that is, both the sensor pair on the arterial side and the sensor pair on the venous side, are evaluated, wherein both terminate the reinfusion on the corresponding side or require a special treatment on the detection of a clot or of an air bubble. The safety clamp is used in every case to stop the blood flow.

FIG. 4 again shows, in a simplified form, the flowchart relating to the signal evaluation of the apparatus or of the method respectively. The signal received by the optical sensor 11 is conducted through a high pass filter and subjected to pulse detection. If an event is detected, it is compared with the signal acquired by the ultrasound sensor 15. If an event was detected essentially simultaneously by both the optical sensor 11 and the ultrasound sensor 15, it is recognized by means of the signal evaluation means, which can, for example, be a component of the central control and/or regulation unit of the blood treatment apparatus, that air bubbles have flowed past.

If an event was only detected by means of the optical sensor 11, it is recognized by means of the signal evaluation means that a clot has flowed past.

Protection and warning means 40 are activated in such a case. In detail, this can, for example, mean that a warning is output on an output means such as on a screen of a blood treatment apparatus in which the apparatus in accordance with the invention is used and that furthermore the extracorporeal blood circuit is optionally stopped.

The invention being thus described, it will be apparent that the same may be varied in many ways. Such variations are not to be regarded as a departure from the spirit and scope of the invention, and all such modifications as would be recognized by one skilled in the art are intended to be included within the scope of the following claims.

What is claimed is:

1. An apparatus for detecting blood clots in a blood stream of an extracorporeal blood circuit, said apparatus comprising:
   at least one optical sensor;
   at least one ultrasound sensor; and
   at least one signal evaluator,
   the apparatus being configured such that the blood is optically monitored by the optical sensor and ultrasonically monitored by the ultrasound sensor, and the signal evaluator being configured such that the blood clots are detected by a comparison of monitoring signals of the optical sensor and of the ultrasound sensor.

2. The apparatus in accordance with claim 1, wherein the blood clots are detected in the blood by the signal evaluator when the optical sensor registers at least one blood clot as a signal-triggering event and the ultrasound sensor substantially simultaneously does not register any blood clot as a signal-triggering event.

3. The apparatus in accordance with claim 1, wherein the blood clots are detectable by the optical sensor and air bubbles are detectable by the ultrasound sensor.

4. The apparatus in accordance with claim 3, wherein the optical sensor has at least one light source and at least one photodetector, and wherein the light source is or includes at least one LED.

5. The apparatus according to claim 4, wherein the light source radiates narrowband, near infrared light with a peak wavelength of approximately 805 nm.

6. The apparatus in accordance with claim 1, further comprising, down-signal of the optical sensor, at least one high pass filter with which the monitoring signal acquired by the optical monitoring is filtered, the high pass filter being a filter with which the monitoring signal is integrated at fixed intervals of a few milliseconds and a floating mean value is determined from a predetermined number of preceding measurements and is subtracted from a current integration result.

7. The apparatus in accordance with claim 4, further comprising a receptacle into which a fluid guidance element or a measurement channel is insertable.

8. The apparatus according to claim 7, wherein the fluid guidance element is at least one of a hose set, a part of a hose set, and a cassette.

9. The apparatus according to claim 8, wherein the cassette is a disposable cassette.

10. The apparatus in accordance with claim 7, wherein the apparatus has or forms a limited measurement path or measurement point at which both the optical sensor and the ultrasound sensor are arranged.

11. The apparatus in accordance with claim 10, wherein the limited measurement path or measurement point is arranged at the receptacle.

12. The apparatus according to claim 11, wherein the limited measurement path or measurement point is surrounded by the light source, by the ultrasound sensor, and by the photodetector on three sides thereof, such that the light source, the ultrasound sensor, and the photodetector surround the limited measurement path or measurement point in a U shape.

13. The apparatus in accordance with claim 1, further comprising at least one of a protection element and a warning element, wherein the blood flow is stoppable by the protection element and wherein attention to the blood clots is effected by the warning element.

14. The apparatus in accordance with claim 1, wherein the apparatus is a component of a blood treatment apparatus or is a blood treatment apparatus.

15. The apparatus in accordance with claim 14, wherein the blood treatment apparatus is a hemodialysis machine.

16. The apparatus according to claim 1, wherein the apparatus is in communication with at least one of a protection element and a warning element, and wherein the blood flow is stoppable by the protection element and wherein attention to the blood clots is effected by the warning element.

17. A method of detecting blood clots in a blood stream of an extracorporeal blood circuit with an apparatus that includes an optical sensor, an ultrasound sensor, and a signal evaluator, said method comprising:

optically monitoring the blood with the optical sensor;

ultrasonically monitoring the blood with the ultrasound sensor; and detecting the blood clots by comparing monitoring signals of the optical sensor and of the ultrasound sensor.

18. The method in accordance with claim 17, wherein the blood clots are detected in the blood by the signal evaluator when the optical sensor registers at least one blood clot as a signal-triggering event and the ultrasound sensor substantially simultaneously does not register any blood clot as a signal-triggering event.

19. The method in accordance with claim 17, wherein the monitoring signal acquired by the optical monitoring is filtered by a high pass filter.

20. The method in accordance with claim 19, wherein the high pass filter is a filter in which the monitoring signal is integrated at fixed intervals of a few milliseconds and a floating mean value is determined from a predetermined number of preceding measurements and is subtracted from a current integration result.

21. The method in accordance with claim 17, wherein the signal evaluator distinguishes a first blood clot from a second blood clot.

* * * * *